United States Patent [19]
Audousset et al.

[11] Patent Number: 6,093,219
[45] Date of Patent: *Jul. 25, 2000

[54] COMPOSITION FOR THE OXIDATION DYEING OF KERATIN FIBERS, COMPRISING AT LEAST TWO OXIDATION BASES AND AN INDOLE COUPLER, AND DYEING PROCESS

[75] Inventors: Marie-Pascale Audousset, Asnieres; Jean Cotteret, Verneuil sur Seine; Roland de la Mettrie, Le Vesinet; Christelle Grimault, Levallois-Perret, all of France

[73] Assignee: L'Oreal, France

[*] Notice: This patent is subject to a terminal disclaimer.

[21] Appl. No.: 09/042,080

[22] Filed: Mar. 13, 1998

Related U.S. Application Data

[63] Continuation of application No. 08/607,721, Feb. 27, 1996, abandoned.

[30] Foreign Application Priority Data

Feb. 27, 1995 [FR] France ................... 95 02269

[51] Int. Cl.$^7$ ........................................ A61K 7/13
[52] U.S. Cl. ..................... 8/409; 8/410; 8/412; 8/423
[58] Field of Search ................. 8/406, 408, 409, 8/410, 412, 423

[56] References Cited

U.S. PATENT DOCUMENTS

| | | | |
|---|---|---|---|
| 5,061,289 | 10/1991 | Clausen et al. .................. | 8/405 |
| 5,131,911 | 7/1992 | Lang et al. ..................... | 8/405 |
| 5,207,798 | 5/1993 | Cotteret et al. ................. | 8/408 |
| 5,354,870 | 10/1994 | Lang et al. ..................... | 548/469 |
| 5,380,340 | 1/1995 | Neunhoeffer et al. ............ | 8/409 |
| 5,391,206 | 2/1995 | Cotteret ......................... | 8/408 |
| 5,609,649 | 3/1997 | Junino et al. ................... | 8/409 |
| 5,683,474 | 11/1997 | Cotteret et al. ................. | 8/409 |
| 5,752,982 | 5/1998 | Lang et al. ..................... | 8/409 |
| 5,769,903 | 6/1998 | Audousset et al. .............. | 8/409 |

FOREIGN PATENT DOCUMENTS

| | | |
|---|---|---|
| 0375977 | 7/1990 | European Pat. Off. . |
| 0428441 | 5/1991 | European Pat. Off. . |
| 0446132 | 9/1991 | European Pat. Off. . |
| 0465339 | 1/1992 | European Pat. Off. . |
| 0465340 | 1/1992 | European Pat. Off. . |
| 0634164 | 1/1995 | European Pat. Off. . |
| 1916139 | 11/1969 | Germany . |
| 3031709 | 4/1982 | Germany . |
| 3743769 | 7/1989 | Germany . |
| 3930446 | 3/1990 | Germany . |
| 4133957 | 4/1993 | Germany . |
| 1217479 | 12/1970 | United Kingdom . |
| 2180215 | 3/1987 | United Kingdom . |
| WO-9309759 | 5/1993 | WIPO . |
| WO-09408970 | 4/1994 | WIPO . |

OTHER PUBLICATIONS

English language translation of EP 465,339, L'Oreal, pp. 1–27, Jan. 1990.
English language translation of EP 428,441, L'Oreal, pp. 1–27, Nov. 1990.
English Derwent Abstract of DE–A–3743769, Jul. 1989.
English Derwent Abstract of DE–A–3031709, Apr. 1982.
English Derwent Abstract of EP–A–0634164, Jan. 1995.
English Derwent Abstract of EP–A–0428441, May 1991.
English Derwent Abstract of EP–A–0465339, Jan. 1992.
English Derwent Abstract of WO–A–9408970, Apr. 1994.

*Primary Examiner*—Caroline D. Liott
*Attorney, Agent, or Firm*—Finnegan, Henderson, Farabow, Garrett & Dunner

[57] ABSTRACT

The present invention relates to a composition for the oxidation dyeing of keratin fibers, in particular human keratin fibers such as the hair, comprising at least two oxidation bases which are different from each other in combination with a suitably selected indole coupler, and to the dyeing process using this composition with an oxidizing agent.

26 Claims, No Drawings

COMPOSITION FOR THE OXIDATION DYEING OF KERATIN FIBERS, COMPRISING AT LEAST TWO OXIDATION BASES AND AN INDOLE COUPLER, AND DYEING PROCESS

This is a continuation of application Ser. No. 08/607,721, filed Feb. 27, 1996, now abandoned.

The present invention relates to a composition for the oxidation dyeing of keratin fibers, in particular human keratin fibers such as the hair, comprising at least two oxidation bases which are different from each other in combination with a suitably selected indole coupler, and to a dyeing process using this composition with an oxidizing agent.

It is known to dye keratin fibers, and in particular human hair, with dye compositions containing oxidation dye precursors, in particular ortho- or para-phenylenediamines, ortho- or para-aminophenols, and heterocyclic compounds such as diaminopyrazole derivatives, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain heterocyclic compounds such as indole derivatives and in particular 4-hydroxyindole. The variety of molecules used as oxidation bases and couplers makes it possible to obtain a wide range of colors.

The so-called "permanent" coloration obtained by means of these oxidation dyes should highly preferably moreover satisfy a certain number of requirements. Thus, it should highly preferably have no toxicological drawbacks and should highly preferebly allow shades of the desired intensity to be obtained and have good resistance to external agents (light, inclement weather, washing, permanent waving, perspiration and friction).

The dyes should highly preferably also allow white hairs to be covered and, lastly, they should highly preferably be as unselective as possible, that is to say that they should highly preferably allow the smallest possible differences in coloration to be produced over the entire length of the same keratin fiber, which may indeed be differently sensitized (i.e. damaged) between its tip and its root.

Compositions for the oxidation dyeing of keratin fibers in an alkaline or acidic medium containing an oxidation base such as para-phenylenediamine or para-aminophenol, in combination with a heterocyclic coupler such as, for example, 4-hydroxyindole, have already been proposed, in particular in patent applications DE 3,031,709 and FR 2,664,304. Such compositions make it possible to achieve varied ranges of shades depending on the nature of the oxidation bases chosen; however, they are not entirely satisfactory, in particular from the point of view of the resistance of the colorations obtained to the various attacking factors to which the hair may be subjected and, in particular, to light.

The inventors have discovered that it is possible to obtain novel dyes by combining at least two suitably selected different oxidation bases and a suitably selected indole coupler, these dyes being capable of giving rise to intense colorations in varied shades, which are quite unselective and particularly resistant, especially with respect to light, shampooing and permanent-waving. This discovery forms the basis of the present invention.

The subject of the invention is thus a composition for the oxidation dyeing of keratin fibers, and in particular human keratin fibers such as the hair, characterized in that it comprises, in a medium which is suitable for dyeing:

a) at least two oxidation bases which are different from each other, b) at least one indole coupler, said indole coupler being of the formula (I), and/or at least one acid addition salt thereof:

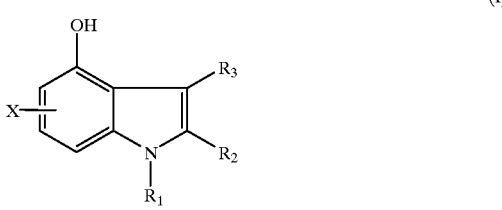

in which:

$R_1$ represents a hydrogen atom or a $C_1$–$C_4$ alkyl radical, $R_2$ and $R_3$, which may be identical or different, represent a hydrogen atom or a $C_1$–$C_4$ alkyl, carboxyl or ($C_1$–$C_4$) alkoxycarbonyl radical, X represents a hydrogen or halogen atom or a $C_1$–$C_4$ alkyl, $C_1$–$C_{18}$ alkoxy or acetylamino radical.

The oxidation dyeing composition in accordance with the invention makes it possible to obtain colorations in varied shades, which are quite unselective and have excellent properties of resistance both to atmospheric agents such as light and inclement weather and to perspiration and the various treatments to which the hair may be subjected (shampooing, permanent-waving). These properties are particularly noteworthy, especially with respect to the resistance of the colorations obtained to light, shampooing and permanent-waving operations.

The subject of the invention is also a process for the oxidation dyeing of keratin fibers using this composition.

The oxidation bases which may be used within the context of the dye compositions in accordance with the invention are preferably chosen from para-phenylenediamines, bis (phenyl)alkylenediamines, para-aminophenols, ortho-aminophenols, heterocyclic bases, and the acid addition salts thereof.

The acid addition salts which may be used in the context of the dye compositions of the invention are chosen in particular from the hydrochlorides, hydrobromides, sulphates and tartrates.

Among the para-phenylenediamines which may be used as oxidation bases in the context of the compositions in accordance with the invention, mention may be made in particular of the compounds corresponding to the following formula (II), and the acid addition salts thereof:

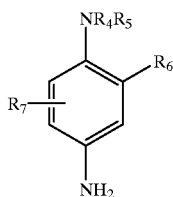

(II)

in which:
R$_4$ represents a hydrogen atom or a C$_1$–C$_4$ alkyl, C$_1$–C$_4$ monohydroxyalkyl, C$_2$–C$_4$ polyhydroxyalkyl or (C$_1$–C$_4$) alkoxy(C$_1$–C$_4$) alkyl radical,
R$_5$ represents a hydrogen atom or a C$_1$–C$_4$ alkyl, C$_1$–C$_4$ monohydroxyalkyl or C$_2$–C$_4$ polyhydroxyalkyl radical,
R$_6$ represents a hydrogen atom, a halogen atom such as a chlorine atom or a C$_1$–C$_4$ alkyl, sulpho, carboxyl, C$_1$–C$_4$ monohydroxyalkyl or C$_1$–C$_4$ hydroxyalkoxy radical,
R$_7$ represents a hydrogen atom or a C$_1$–C$_4$ alkyl radical.

In the above para-phenylenediamine formula (II), and when R$_7$ is other than a hydrogen atom, R$_4$ and R$_5$ then preferably represent a hydrogen atom and R$_6$ is preferably identical to R$_7$, and when R$_6$ represents a halogen atom, R$_4$, R$_5$ and R$_7$ then preferably represent a hydrogen atom.

Among the para-phenylenediamines of above formula (II) which may be mentioned more particularly are para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl)aminobenzene, 2-chloro-para-phenylenediamine, and the acid addition salts thereof.

Among the bis(phenyl)alkylenediamines which may be used as oxidation bases in the context of the compositions in accordance with the invention, mention may more particularly be made of the compounds corresponding to the following formula (Ill), and the acid addition salts thereof:

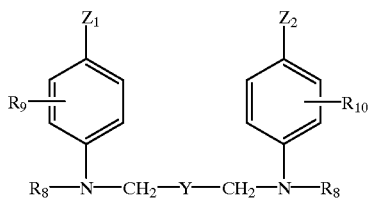

(III)

in which:
Z$_1$ and Z$_2$, which may be identical or different, represent a hydroxyl radical or a radical NHR$_{11}$ in which R$_{11}$ represents a hydrogen atom or a C$_1$–C$_4$ alkyl radical,
R$_8$ independently represents a hydrogen atom or a C$_1$–C$_4$ alkyl, C$_1$–C$_4$ monohydroxyalkyl or C$_2$–C$_4$ polyhydroxyalkyl radical or a C$_1$–C$_4$ aminoalkyl radical in which the amino residue may be substituted,
R$_9$ and R$_{10}$, which may be identical or different, represent a hydrogen or halogen atom or a C$_1$–C$_4$ alkyl radical,
Y represents a radical selected from the following radicals: —(CH$_2$)$_n$—; —(CH$_2$)$_m$—O—(CH$_2$)$_m$—; —(CH$_2$)$_m$—CHOH—(CH$_2$)$_m$— and

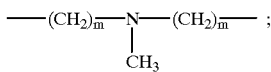

in which n is an integer from 0 to 8 and m is an integer independently from 0 to 4.

Among the bis(phenyl)alkylenediamines of above formula (III) which may be mentioned more particularly are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and the acid addition salts thereof.

Among these bis(phenyl)alkylenediamines of formula (III), N,N'-bis(β-hydroxyethyl)-N,N'-bis(4'-aminophenyl)-1,3-diaminopropanol or one of the acid addition salts thereof is particularly preferred.

Among the para-aminophenols which may be used as oxidation bases in the context of the compositions in accordance with the invention, mention may more particularly be made of the compounds corresponding to the following formula (IV), and the acid addition salts thereof:

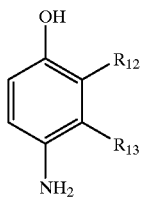

(IV)

in which:
R$_{12}$ represents a hydrogen atom or a C$_1$–C$_4$ alkyl, C$_1$–C$_4$ monohydroxyalkyl, (C$_1$–C$_4$)alkoxy(C$_1$–C$_4$) alkyl or C$_1$–C$_4$ aminoalkyl radical,
R$_{13}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy (C$_1$–C$_4$) alkyl radical,
it being understood that at least one of the radicals R$_{12}$ or R$_{13}$ represents a hydrogen atom.

Among the para-aminophenols of above formula (IV) which may more particularly be mentioned are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and the acid addition salts thereof.

Among the ortho-aminophenols which may be used as oxidation bases in the context of the compositions in accordance with the invention, there may more particularly be mentioned 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases which may be used as oxidation bases in the context of the compositions in accordance with the invention, there may more particularly be mentioned pyridine derivatives, pyrimidine derivatives, pyrazole derivatives, and the acid addition salts thereof.

Among the pyridine derivatives which may more particularly be mentioned are the compounds described, for example, in GB patents 1,026,978 and 1,153,196, the disclosures of which are hereby incorporated by reference in their entirety, such as 2,5-diaminopyridine, and the acid addition salts thereof.

Among the pyrimidine derivatives which may more particularly be mentioned are the compounds described, for example, in German patent DE 2,359,399 or Japanese patents JP 88-169,571 and JP 91-333,495, the disclosures of which are hereby incorporated by reference in their entirety, such as 2,4,5,6-tetraaminopyrimidine, 4-hydroxy-2,5,6-triaminopyrimidine, and the acid addition salts thereof.

Among the pyrazole derivatives which may more particularly be mentioned are the compounds described in patents DE 3,843,892 and DE 4,133,957 and patent applications WO 94108969 and WO 94/08970, the disclosures of which are hereby incorporated by reference in their entirety, such as 4,5-diamino-1-methylpyrazole, 3,4-diaminopyrazole, and the acid addition salts thereof.

Among the indole couplers of above formula (I) which may more particularly be mentioned are 4-hydroxyindole, 4-hydroxy-5-ethoxyindole, 4-hydroxy-5-methoxyindole, 4-hydroxy-1-methyl-5-ethoxyindole, 4-hydroxy-2-ethoxycarbonyl-5-ethoxyindole, 4-hydroxy-2-methyl-5-ethoxyindole, 4-hydroxy-5-methylindole, 4-hydroxy-2-methylindole, 4-hydroxy-1-methylindole, and the acid addition salts thereof.

According to a particularly preferred embodiment of the invention, the oxidation dye compositions in accordance with the invention include at least one of the following ternary combinations:

($a_1$): para-phenylenediamine,
($a_2$): para-aminophenol,
(b): 4-hydroxyindole;
($a_1$): para-phenylenediamine,
($a_2$): 4-amino-3-methylphenol,
(b): 4-hydroxyindole;
($a_1$): para-aminophenol,
($a_2$): 4-amino-3-methylphenol,
(b): 4-hydroxyindole;
($a_1$): 2,6-dimethyl-para-phenylenediamine,
($a_2$): para-aminophenol,
(b): 4-hydroxyindole;
($a_1$): 2,6-dimethyl-para-phenylenediamine,
($a_2$): 4-amino-3-methylphenol,
(b): 4-hydroxyindole;
($a_1$): 2-β-hydroxyethyl-para-phenylenediamine,
($a_2$): para-aminophenol,
(b): 4-hydroxyindole;
($a_1$): 2-β-hydroxyethyl-para-phenylenediamine,
($a_2$): 4-amino-3-methylphenol,
(b): 4-hydroxyindole;
($a_1$): N,N-bis(β-hydroxyethyl)-para-phenylenediamine,
($a_2$): para-aminophenol,
(b): 4-hydroxyindole;
($a_1$): N,N-bis(β-hydroxyethyl)-para-phenylenediamine,
($a_2$): 4-amino-3-methylphenol,
(b): 4-hydroxyindole;
($a_1$): para-toluylenediamine,
($a_2$): para-aminophenol,
(b): 4-hydroxyindole;
($a_1$): para-toluylenediamine,
($a_2$): 4-amino-3-methylphenol,
(b): 4-hydroxyindole;
($a_1$): para-phenylenediamine,
($a_2$): 4-amino-3-fluorophenol,
(b): 4-hydroxyindole;
($a_1$): 2,6-dimethyl-para-phenylenediamine,
($a_2$): 4-amino-3-fluorophenol,
(b): 4-hydroxyindole;
($a_1$): 2-β-hydroxyethyl-para-phenylenediamine,
($a_2$): 2,6-dimethyl-para-phenylenediamine,
(b): 4-hydroxyindole;
($a_1$): 2-β-hydroxyethyl-para-phenylenediamine,
($a_2$): 4-amino-3-fluorophenol,
(b): 4-hydroxyindole;
($a_1$): N,N-bis(β-hydroxyethyl)-para-phenylenediamine,
($a_2$): 4-amino-3-fluorophenol,
(b): 4-hydroxyindole;
($a_1$): para-toluylenediamine,
($a_2$): 4-amino-3-fluorophenol,
(b): 4-hydroxyindole;
($a_1$): 4-amino-3-fluorophenol,
($a_2$): 4-amino-3-methylphenol,
(b): 4-hydroxyindole;
($a_1$): para-phenylenediamine,
($a_2$): 2-aminophenol,
(b): 4-hydroxyindole;
($a_1$): para-aminophenol,
($a_2$): 2-aminophenol,
(b): 4-hydroxyindole;
($a_1$): para-toluylenediamine,
($a_2$): 2-aminophenol,
(b): 4-hydroxyindole;
($a_1$): 2,6-dimethyl-para-phenylenediamine,
($a_2$): 2-aminophenol,
(b): 4-hydroxyindole;
($a_1$): 2-β-hydroxyethyl-para-phenylenediamine,
($a_2$): 2-aminophenol,
(b): 4-hydroxyindole;
($a_1$): N,N-bis(β-hydroxyethyl)-para-phenylenediamine,
($a_2$): 2-aminophenol,
(b): 4-hydroxyindole;
($a_1$): 4-amino-3-methylphenol,
($a_2$): 2-aminophenol,
(b): 4-hydroxyindole;
($a_1$): 4-amino-3-fluorophenol,
($a_2$): 2-aminophenol,
(b): 4-hydroxyindole;
($a_1$): para-phenylenediamine,
($a_2$): para-aminophenol,
(b): 4-hydroxy-1-methylindole;
($a_1$): para-phenylenediamine,
($a_2$): 4-amino-3-methylphenol,
(b): 4-hydroxy-1-methylindole;
($a_1$): 2,6-dimethyl-para-phenylenediamine,
($a_2$): para-aminophenol,
(b): 4-hydroxy-1-methylindole;
($a_1$): 2,6-dimethyl-para-phenylenediamine,
($a_2$): 4-amino-3-methylphenol,
(b): 4-hydroxy-1-methylindole;
($a_1$): 2-methyl-para-phenylenediamine,
($a_2$): para-aminophenol,
(b): 4-hydroxy-1-methylindole;
($a_1$): 2-methyl-para-phenylenediamine,
($a_2$): 4-amino-3-methylphenol,
(b): 4-hydroxy-1-methylindole;
($a_1$): para-phenylenediamine,
($a_2$): 4-amino-3-fluorophenol,
(b): 4-hydroxy-1-methylindole;
($a_1$): para-phenylenediamine,
($a_2$): N,N'-bis(β-hydroxyethyl)-N,N'-bis(4'-aminophenyl)-1,3-diamino-2-propanol, (b): 4-hydroxyindole;
($a_1$): para-phenylenediamine,
($a_2$): N,N-bis(hydroxyethyl)-para-phenylenediamine
(b): 4-hydroxyindole;
($a_1$): 2,6-dimethyl-para-phenylenediamine,
($a_2$): N,N-bis(hydroxyethyl)-para-phenylenediamine
(b): 4-hydroxyindole;
($a_1$): para-phenylenediamine,
($a_2$): 4-amino-3-hydroxymethylphenol,
(b): 4-hydroxyindole;
($a_1$): 2,6-dimethyl-para-phenylenediamine,
($a_2$): 4-amino-3-hydroxymethylphenol,
(b): 4-hydroxyindole;
($a_1$): para-phenylenediamine,
($a_2$): N,N'-bis(β-hydroxyethyl)-N,N'-bis(4'-aminophenyl)-1, 3-diamino-2-propanol,
(b): 4-hydroxy-1-methylindole;
($a_1$): para-phenylenediamine,
($a_2$): N,N-bis(hydroxyethyl)-para-phenylenediamine,
(b): 4-hydroxy-1-methylindole;
($a_1$): 2,6-dimethyl-para-phenylenediamine,
($a_2$): N,N-bis(hydroxyethyl)-para-phenylenediamine,
(b): 4-hydroxy-1-methylindole;
($a_1$): para-phenylenediamine,
($a_2$): 4-amino-3-hydroxymethylphenol,
(b): 4-hydroxy-1-methylindole;
($a_1$): 2,6-dimethyl-para-phenylenediamine,
($a_2$): 4-amino-3-hydroxymethylphenol,
(b): 4-hydroxy-1-methylindole.

The oxidation bases in accordance with the invention together preferably represent approximately from 0.0005 to 12% by weight relative to the total weight of the dye composition, and even more preferably approximately from 0.005 to 6% by weight relative to this weight.

The indole coupler or couplers of formula (I) in accordance with the invention preferably represent approximately from 0.0001 to 5% by weight relative to the total weight of the dye composition and even more preferably approximately from 0.005 to 3% by weight relative to this weight.

The appropriate medium for the dyeing (or the support) generally consists of water or of a mixture of water and at least one organic solvent to solubilize the compounds which would not be sufficiently soluble in water. Organic solvents which may be mentioned, for example, are $C_1-C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxyethanol, similar products and mixtures thereof.

The solvents may be present in proportions preferably of approximately from 1 to 40% by weight relative to the total weight of the dye composition, and even more preferably of approximately from 5 to 30% by weight.

The pH of the dye composition in accordance with the invention is generally approximately from 3 to 12 and even more preferably approximately from 5 to 11. It may be adjusted to the desired value using acidifying or basifying agents usually used in the dyeing of keratin fibers.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of following formula (V)

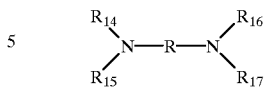

in which R is a propylene residue optionally substituted with a hydroxyl group or a $C_1-C_4$ alkyl radical; $R_{14}, R_{15}, R_{16}$ and $R_{17}$, which may be identical or different, represent a hydrogen atom or a $C_1-C_4$ alkyl or $C_1-C_4$ hydroxyalkyl radical.

In addition to the dyes defined above, the dye composition in accordance with the invention may also contain other oxidation bases and/or other couplers and/or direct dyes, in particular in order to modify the shades or to enrich them with glints.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to choose this or these optional complementary compound(s) such that the advantageous properties intrinsically associated with the ternary combination in accordance with the invention are not, or are substantially not, adversely affected by the addition or additions envisaged.

The dye composition according to the invention may be in various forms, such as in the form of liquids, creams, gels or any other form which is suitable for dyeing keratin fibers, and in particular human hair.

Another subject of the invention is a process for dyeing keratin fibers, and in particular human keratin fibers such as the hair, using the dye composition as defined above.

According to this process, the dye composition as defined above is applied to the fibers, the color being developed at acidic, neutral or alkaline pH using an oxidizing agent which is added only at the time of use to the dye composition or which is present in an oxidizing composition that is applied simultaneously or sequentially in a separate manner, i.e., the oxidizing composition is applied from a separate dispenser than the dye composition, either at the same time (simultaneously) as the dye composition or sequentially with it.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibers and is left in place for 3 to 50 minutes approximately, preferably 5 to 30 minutes approximately, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibers preferably varies approximately from 3 to 12 and even more preferably approximately from 5 to 11. It is adjusted to the desired value using acidifying or basifying agents usually used in the dyeing of keratin fibers and as are defined above.

The oxidizing composition as defined above may also include various adjuvants used conventionally in compositions for dyeing the hair and as are defined above.

The composition which is finally applied to the keratin fibers may be in various forms, such as in the form of liquids, creams, gels or any other form which is suitable for dyeing keratin fibers, and in particular human hair.

Another subject of the invention is a multi-compartment device or dyeing "kit" or any other multi-compartment packaging system a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913 in the name of the present assignee.

The examples which follow are intended to illustrate the invention without, however, limiting the scope thereof.

EXAMPLES

Examples 1 to 4 of Dyeing in an Alkaline Medium

The following dye compositions in accordance with the invention were prepared (contents in grams):

|  | EXAMPLE | | | |
|---|---|---|---|---|
|  | 1 | 2 | 3 | 4 |
| 2,6-Dimethyl-para-phenylenediamine dihydrochloride | 0.2 | | | |
| Para-aminophenol | 0.2 | 0.2 | 0.3 | |
| 2-Aminophenol | | 0.2 | | |
| 2-β-Hydroxyethyl-para-phenylenediamine dihydrochloride | | | 0.3 | |
| 4-Amino-3-fluorophenol | | | | 0.15 |
| Para-phenylenediamine | | | | 0.15 |
| 4-Hydroxyindole | 0.4 | 0.3 | 0.6 | |
| 4-Hydroxy-1-methylindole | | | | 0.35 |
| Common dye support | (*) | (*) | (*) | (*) |
| Demineralized water qs. | 100 g | 100 g | 100 g | 100 g |

(*): Common dye support:

| Oleyl alcohol polyglycerolated with 2 mol of glycerol | 4.0 g | |
| --- | --- | --- |
| Oleyl alcohol polyglycerolated with 4 mol of glycerol, containing 78% of active material (AM) | 5.69 g | AM |
| Oleic acid | 3.0 g | |
| Oleylamine containing 2 mol of ethylene oxide, sold under the trade name Ethomeen O12 by the company AKZO | 7.0 g | |
| Diethylaminopropyl laurylaminosuccinamate, sodium salt, containing 55% of AM | 3.0 g | AM |
| Oleyl alcohol | 5.0 g | |
| Oleic acid diethanolamide | 12.0 g | |
| Propylene glycol | 3.5 g | |
| Ethyl alcohol | 7.0 g | |

-continued

| Dipropylene glycol | 0.5 g | |
| --- | --- | --- |
| Propylene glycol monomethyl ether | 9.0 g | |
| Sodium metabisulphite in aqueous solution, containing 35% of AM | 0.455 g | AM |
| Ammonium acetate | 0.8 g | |
| Antioxidant, sequestering agent | qs | |
| Fragrance, preserving agent | qs | |
| Aqueous ammonia containing 20% of $NH_3$ | 10.0 g | |

Each dye composition was mixed, at the time of use, with an equal weight amount of 20-volumes aqueous hydrogen peroxide solution (6% by weight).

Each resulting composition had a pH of approximately 10.2, and was applied for 30 minutes to locks of natural or permanent-waved grey hair containing 90% white hairs. The locks of hair were then rinsed, washed with a standard shampoo and then dried.

The locks of hair were dyed in the shades featured in the table below:

| EXAMPLE | SHADE ON NATURAL HAIR | SHADE ON PERMANENT-WAVED HAIR |
| --- | --- | --- |
| 1 | Slightly coppery iridescent purplish-blue | Slightly purplish-blue iridescent |
| 2 | Slightly coppery iridescent | Slightly coppery purplish-blue iridescent |
| 3 | Slightly violet iridescent | Iridescent violet |
| 4 | Violet ash | Violet |

Example 5 of Dying in an Acidic Medium

The following dye composition in accordance with the invention was prepared (contents in grams):

|  | EXAMPLE 5 |
| --- | --- |
| 2-β-Hydroxyethyl-para-phenylenediamine dihydrochloride | 0.05 |
| 2,6-Dimethyl-para-phenylenediamine dihydrochloride | 0.05 |
| 4-Hydroxyindole | 0.1 |
| Common dye support | (**) |
| Demineralized water qs | 100 g |

(**): Dye support:

| Oleyl alcohol polyglycerolated with 2 mol of glycerol | 4.0 g | |
| --- | --- | --- |
| Oleyl alcohol polyglycerolated with 4 mol of glycerol, containing 78% of active material (AM) | 5.69 g | AM |
| Oleic acid | 3.0 g | |
| Oleylamine containing 2 mol of ethylene oxide, sold under the trade name Ethomeen O12 by the company AKZO | 7.0 g | |
| Diethylaminopropyl laurylaminosuccinamate, sodium salt, containing 55% of AM | 3.0 g | AM |
| Oleyl alcohol | 5.0 g | |
| Oleic acid diethanolamide | 12.0 g | |
| Propylene glycol | 3.5 g | |
| Ethyl alcohol | 7.0 g | |

-continued

| | |
|---|---|
| Dipropylene glycol | 0.5 g |
| Propylene glycol monomethyl ether | 9.0 g |
| Sodium metabisulphite in aqueous solution, containing 35% of AM | 0.455 g AM |
| Ammonium acetate | 0.8 g |
| Antioxidant, sequestering agent | qs |
| Fragrance, preserving agent | qs |
| Monoethanolamine qs | pH 9.8 |

The dye composition was mixed, at the time of use, with an equal weight amount of 20-volumes aqueous hydrogen peroxide solution (6% by weight), the pH of which had been adjusted to between 1 and 1.5 with 2.5 g of orthophosphoric acid per 100 g of aqueous hydrogen peroxide solution.

The resulting composition had a pH of 6.5, and was applied for 30 minutes to locks of natural or permanent-waved grey hair containing 90% white hairs. The locks of hair were then rinsed, washed with a standard shampoo and then dried.

The locks of hair were dyed in the shades featured in the table below:

| EXAMPLE | SHADE ON NATURAL HAIR | SHADE ON PERMANENT-WAVED HAIR |
|---|---|---|
| 5 | Ashen natural grey | Slightly bluish natural grey |

Comparative Example 6

The following dye compositions were prepared (contents in grams):

| | COMPOSITION | | |
|---|---|---|---|
| | A1 | A2 | A3 |
| Para-aminophenol | 0.3 | | 0.15 |
| Para-phenylenediamine | | 0.3 | 0.15 |
| 4-Hydroxyindole | 0.3 | 0.3 | 0.3 |
| Common dye support | (*) | (*) | (*) |
| Demineralized water qs | 100 g | 100 g | 100 g |

(*): Common dye support identical to that used in Examples 1 to 4 above.

Compositions A1 and A2 do not form part of the invention.

Composition A3 is in accordance with the invention.

Each dye composition was mixed, at the time of use, with an equal weight amount of 20-volumes aqueous hydrogen peroxide solution (6% by weight).

Each resulting composition had a pH of about 10.2, and was applied for 30 minutes to locks of natural grey hair containing 90% white hairs. The locks of hair were then rinsed, washed with a standard shampoo and then dried.

The color of the locks was then evaluated in the Munsell system using a Minolta CM 2002 calorimeter.

According to the Munsell notation, a color is defined by the expression HV/C in which the three parameters respectively denote the shade or Hue (H), the intensity or Value (V) and the purity or Chromaticity (C), the oblique line in this expression simply being a convention and not indicating a ratio.

The locks of hair thus dyed were then subjected to a test of resistance to washing (Ahiba-Texomat machine).

To do this, the locks of hair were placed in a basket which is immersed in a solution of a standard shampoo at 37° C. The basket was subjected to an up-and-down motion of variable frequency as well as to a rotational motion, which reproduced the action of manual rubbing, thereby causing the formation of foam.

After a test time of 3 minutes, the locks were removed and then rinsed and dried. The dyed locks were subjected to 5 consecutive shampooing tests.

The color of the locks was then re-evaluated in the Munsell system using a Minolta CM 2002 calorimeter.

The difference between the color of the lock before the shampooings and the color of the lock after the shampooings was calculated by applying the Nickerson formula:

$\Delta E = 0.4\ C_0 \Delta H + 6 \Delta V + 3 \Delta C$, as described, for example, in "Couleur, Industrie et Technique"; pages 14–17; vol. No. 5; 1978.

In this formula, $\Delta E$ represents the difference in color between two locks, $\Delta H$, $\Delta V$ and $\Delta C$ represent the variation in absolute value of the parameters H, V and C, and $C_0$ represents the purity of the lock relative to which it is desired to evaluate the color difference.

The results are given in the table below:

| COMPOSITION | Color of the hair before the shampooings | Color of the hair after the shampooings | Degradation of the color | | | |
|---|---|---|---|---|---|---|
| | | | ΔH | ΔV | ΔC | ΔE |
| A1 | 7.4 R 3.9/4.0 | 8.4 R 4.2/3.3 | 1.0 | 0.3 | 0.7 | 5.5 |
| A2 | 8.5 P 2.6/1.7 | 0.4 RP 3.0/1.3 | 1.9 | 0.4 | 0.4 | 4.9 |
| A3 | 2.9 R 3.2/2.0 | 2.3 R 3.4/1.9 | 0.6 | 0.2 | 0.1 | 2.0 |

These results show that the composition A3 in accordance with the invention, that is to say comprising at least two oxidation bases (para-phenylenediamine and para-aminophenol), in combination with 4-hydroxyindole as coupler, leads to a coloration which resists shampooing better than the colorations obtained with the compositions A1 and A2 as described, for example, in patent application DE 3,031,709 and which do not form part of the invention since they each contain only one of these two oxidation bases.

Comparative Example 7

The following dye compositions were prepared (contents in grams):

| | COMPOSITION | |
|---|---|---|
| | A4 | A5 |
| Para-aminophenol | 0.3 | 0.15 |
| Para-phenylenediamine | | 0.15 |
| 4-Hydroxyindole | 0.3 | 0.3 |
| Common dye support | () | () |
| Demineralized water qs | 100 g | 100 g |

(**): Common dye support identical to that used in Example 5 above.

Compositions A4 does not form part of the invention.

Composition A5 is in accordance with the invention.

Each dye composition was mixed, at the time of use, with an equal weight amount of 20-volumes aqueous hydrogen peroxide solution (6% by weight), the pH of which had been adjusted to between 1 and 1.5 with 2.5 g of orthophosphoric acid per 100 g of aqueous hydrogen peroxide solution.

Each resulting composition had a pH of 6.5, and was applied for 30 minutes to locks of permanent-waved grey hair containing 90% white hairs. The locks of hair were then rinsed, washed with a standard shampoo and then dried.

The color of the locks was then evaluated in the Munsell system using a Minolta CM 2002 calorimeter, in order to determine the power of the coloration obtained.

The results are given in the table below:

| COMPO-SITION | Color of the hair before the dyeing | Color of the hair after the dyeing | Power of the coloration | | | |
|---|---|---|---|---|---|---|
| | | | ΔH | ΔV | ΔC | ΔE |
| A4 | 4.4 Y 5.4/1.5 | 7.5 YR 4.7/2.5 | 6.9 | 0.7 | 1.0 | 11.3 |
| A5 | 4.4 Y 5.4/1.5 | 9.3 RP 2.6/1.0 | 25.1 | 2.8 | 0.5 | 33.4 |

These results show that the composition A5 in accordance with the invention, that is to say comprising at least two oxidation bases (para-phenylenediamine and para-aminophenol), in combination with 4-hydroxyindole as coupler, leads to a much more powerful coloration than the coloration obtained with the composition A4 as described, for example, in patent application FR 2,664,304 and which does not form part of the invention since it contains only one of these two oxidation bases, namely para-aminophenol.

Comparative Example 8

The following dye compositions were prepared (contents in grams):

| | COMPOSITION | |
|---|---|---|
| | A6 | A7 |
| Para-aminophenol | | 0.15 |
| Para-phenylenediamine | 0.3 | 0.15 |
| 4-Hydroxyindole | 0.3 | 0.3 |
| Common dye support | () | () |
| Demineralized water qs | 100 g | 100 g |

(**): Dye support identical to that used in Example 5 above.

Composition A6 does not form part of the invention.

Composition A7 is in accordance with the invention.

Each dye composition was mixed, at the time of use, with an equal weight amount of 20-volumes aqueous hydrogen peroxide solution (6% by weight), the pH of which had been adjusted to between 1 and 1.5 with 2.5 g of orthophosphoric acid per 100 g of aqueous hydrogen peroxide solution.

Each resulting composition had a pH of 6.5, and was applied for 30 minutes to locks of permanent-waved grey hair containing 90% white hairs. The locks of hair were then rinsed, washed with a standard shampoo and then dried.

The color of the locks was then evaluated in the Munsell system using a Minolta CM 2002 calorimeter.

The dyed locks were then subjected to a test of resistance to permanent-waving. To do this, the locks were immersed in a commercial permanent-wave reducing solution, containing 9% by weight of thioglycolic acid, for 15 minutes; the locks were rinsed; they were then soaked in a fixing solution (8-volumes aqueous hydrogen peroxide solution) for 5 minutes. The locks were then rinsed with water, washed with a standard shampoo, rinsed with water and dried.

The color of the locks was then re-evaluated in the Munsell system using a Minolta CM 2002 calorimeter, in order to determine the degradation of the coloration following permanent-waving.

The results are featured in the table below:

| COMPO-SITION | Color of the hair before permanent-waving | Color of the hair after permanent-waving | Degradation of the coloration | | | |
|---|---|---|---|---|---|---|
| | | | ΔH | ΔV | ΔC | ΔE |
| A6 | 6.8 P 2.0/1.1 | 9.7 P 2.5/1.2 | 2.9 | 0.5 | 0.1 | 4.6 |
| A7 | 9.3 RP 2.6/1.0 | 0.3 R 2.7/1.0 | 1.0 | 0.1 | 0 | 1.0 |

These results show that the composition A7 in accordance with the invention, comprising at least two oxidation bases (para-phenylenediamine and para-aminophenol), in combination with 4-hydroxyindole as coupler, leads to a coloration which is much more resistant to permanent-waving than the coloration obtained with the composition A6 as described, for example, in patent application FR 2,664,304 and which does not form part of the invention since it contains only one of these two oxidation bases, namely para-phenylenediamine.

What is claimed is:

1. A composition for the oxidation dyeing of keratin fibers, said composition comprising, in a medium which is suitable for dyeing:
    a) at least two oxidation bases which are different from each other,
    b) at least one indole coupler chosen from compounds of formula (I) and acid addition salts thereof:

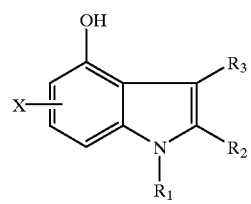

(I)

in which:
    $R_1$ is chosen from a hydrogen atom and $C_1$–$C_4$ alkyl radicals,
    $R_2$ and $R_3$, which may be identical or different, are chosen from a hydrogen atom, $C_1$–$C_4$ alkyl radicals, carboxyl radicals and ($C_1$–$C_4$)alkoxycarbonyl radicals,
    X is chosen from a hydrogen atom, halogen atoms, $C_1$–$C_4$ alkyl radicals, $C_1$–$C_{18}$ alkoxy radicals, and acetylamino radicals,
    wherein said at least two oxidation bases and said at least one indole coupler are present in said composition in a combined amount effective for the oxidation dyeing of keratin fibers.

2. A composition according to claim 1, wherein said at least two oxidation bases are selected from para-phenylenediamines, bis(phenyl)alkylenediamines, para-aminophenols, ortho-aminophenols, heterocyclic bases, and the acid addition salts thereof.

3. A composition according to claim 2, wherein said para-phenylenediamines are selected from the compounds corresponding to the following formula (II), and the acid addition salts thereof:

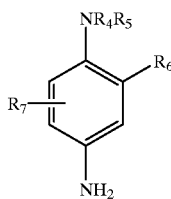

(II)

in which:

R$_4$ represents a hydrogen atom or a C$_1$–C$_4$ alkyl, C$_1$–C$_4$ monohydroxyalkyl, C$_2$–C$_4$ polyhydroxyalkyl or (C$_1$–C$_4$)alkoxy(C$_1$–C$_4$) alkyl radical, R$_5$ represents a hydrogen atom or a C$_1$–C$_4$ alkyl, C$_1$–C$_4$ monohydroxyalkyl or C$_2$–C$_4$ polyhydroxyalkyl radical, R$_6$ represents a hydrogen atom, a halogen atom or a C$_1$–C$_4$ alkyl, sulpho, carboxyl, C$_1$–C$_4$ monohydroxyalkyl or C$_1$–C$_4$ hydroxyalkoxy radical, R$_7$ represents a hydrogen atom or a C$_1$–C$_4$ alkyl radical.

4. A composition according to claim 3, wherein said para-phenylenediamines of formula (II) are selected from para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl) aminobenzene, 2-chloro-para-phenylenediamine, and the acid addition salts thereof.

5. A composition according to claim 2, wherein said bis(phenyl)alkylenediamines are selected from the compounds corresponding to the following formula (III), and the acid addition salts thereof:

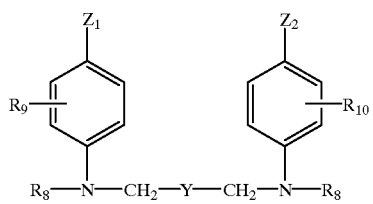

(III)

in which:

Z$_1$ and Z$_2$, which may be identical or different, represent a hydroxyl radical or a radical NHR$_{11}$ in which R$_{11}$ represents a hydrogen atom or a C$_1$–C$_4$ alkyl radical, R$_8$ independently represents a hydrogen atom or a C$_1$–C$_4$ alkyl, C$_1$–C$_4$ monohydroxyalkyl or C$_2$–C$_4$ polyhydroxyalkyl radical or a C$_1$–C$_4$ aminoalkyl radical in which the amino residue may be substituted, R$_9$ and R$_{10}$, which may be identical or different, represent a hydrogen or halogen atom or a C$_1$–C$_4$ alkyl radical, Y represents a radical selected from the following radicals:

—(CH$_2$)$_n$—;  —(CH$_2$)$_m$—O—(CH$_2$)$_m$—;  —(CH$_2$)$_m$—CHOH—(CH$_2$)$_m$— and

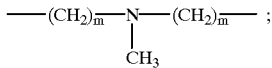

in which n is an integer from 0 to 8 and m is independently an integer from 0 to 4.

6. A composition according to claim 5, wherein said bis(phenyl)alkylenediamines of formula (III) are selected from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and the acid addition salts thereof.

7. A composition according to claim 2, wherein the para-aminophenols are selected from the compounds corresponding to the following formula (IV), and the acid addition salts thereof:

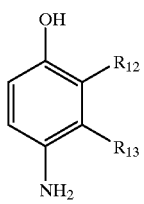

(IV)

in which:

R$_{12}$ represents a hydrogen atom or a C$_1$–C$_4$ alkyl, C$_1$–C$_4$ monohydroxyalkyl, (C$_1$–C$_4$)alkoxy(C$_1$–C$_4$) alkyl or C$_1$–C$_4$ aminoalkyl radical, R$_{13}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$) alkyl radical, it being understood that at least one of the radicals R$_{12}$ and R$_{13}$ represents a hydrogen atom.

8. A composition according to claim 7, wherein said para-aminophenols of formula (IV) are selected from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and the acid addition salts thereof.

9. A composition according to claim 2, wherein said ortho-aminophenols are selected from 2-aminophenol, 2-amino-1-hydroxy-5-methylbenzene, 2-amino-1-hydroxy-6-methylbenzene, 5-acetamido-2-aminophenol, and the acid addition salts thereof.

10. A composition according to claim 2, wherein said heterocyclic bases are selected from pyridine derivatives, pyrimidine derivatives, pyrazoline derivatives, and the acid addition salts thereof.

11. A composition according to claim 10, wherein said heterocyclic oxidation bases are selected from 2,5-diaminopyridine, 2,4,5,6-tetraaminopyridine, 4-hydroxy-2,5,6-triaminopyrimidine, 4,5-diamino-1-methylpyrazole, 3,4-diaminopyrazole, and the acid addition salts thereof.

12. A composition according to claim 1, wherein said at least one indole coupler of formula (I) is selected from 4-hydroxy-indole, 4-hydroxy-5-ethoxyindole, 4-hydroxy-5-methoxy-indole, 4-hydroxy-1-methyl-5-ethoxyindole, 4-hydroxy-2-ethoxycarbonyl-5-ethoxyindole, 4-hydroxy-2-methyl-5-ethoxyindole, 4-hydroxy-5-methylindole, 4-hydroxy-2-methylindole, 4-hydroxy-1-methylindole, and the acid addition salts thereof.

13. A composition according to claim 1, wherein said at least one addition salt with an acid is selected from the hydrochlorides, hydrobromides, sulphates and tartrates.

14. A composition according to claim 1, wherein said composition contains at least one of the following ternary combinations:

($a_1$): para-phenylenediamine,
($a_2$): para-aminophenol,
(b): 4-hydroxyindole;
($a_1$): para-phenylenediamine,
($a_2$): 4-amino-3-methylphenol,
(b): 4-hydroxyindole;
($a_1$): para-aminophenol,
($a_2$): 4-amino-3-methylphenol,
(b): 4-hydroxyindole;
($a_1$): 2,6-dimethyl-para-phenylenediamine,
($a_2$): para-aminophenol,
(b): 4-hydroxyindole;
($a_1$): 2,6-dimethyl-para-phenylenediamine,
($a_2$): 4-amino-3-methylphenol,
(b): 4-hydroxyindole;
($a_1$): 2-β-hydroxyethyl-para-phenylenediamine,
($a_2$): para-aminophenol,
(b): 4-hydroxyindole;
($a_1$): 2-β-hydroxyethyl-para-phenylenediamine,
($a_2$): 4-amino-3-methylphenol,
(b): 4-hydroxyindole;
($a_1$): N,N-bis(β-hydroxyethyl)-para-phenylenediamine,
($a_2$): para-aminophenol,
(b): 4-hydroxyindole;
($a_1$): N,N-bis(β-hydroxyethyl)-para-phenylenediamine,
($a_2$): 4-amino-3-methylphenol,
(b): 4-hydroxyindole;
($a_1$): para-toluylenediamine,
($a_2$): para-aminophenol,
(b): 4-hydroxyindole;
($a_1$): para-toluylenediamine,
($a_2$): 4-amino-3-methylphenol,
(b): 4-hydroxyindole;
($a_1$): para-phenylenediamine,
($a_2$): 4-amino-3-fluorophenol,
(b): 4-hydroxyindole;
($a_1$): 2,6-dimethyl-para-phenylenediamine,
($a_2$): 4-amino-3-fluorophenol,
(b): 4-hydroxyindole;
($a_1$): 2-β-hydroxyethyl-para-phenylenediamine,
($a_2$): 2,6-dimethyl-para-phenylenediamine,
(b): 4-hydroxyindole;
($a_1$): 2-β-hydroxyethyl-para-phenylenediamine,
($a_2$): 4-amino-3-fluorophenol,
(b): 4-hydroxyindole;
($a_1$): N,N-bis(β-hydroxyethyl)-para-phenylenediamine,
($a_2$): 4-amino-3-fluorophenol,
(b): 4-hydroxyindole;
($a_1$): para-toluylenediamine,
($a_2$): 4-amino-3-fluorophenol,
(b): 4-hydroxyindole;
($a_1$): 4-amino-3-fluorophenol,
($a_2$): 4-amino-3-methylphenol,
(b): 4-hydroxyindole;
($a_1$): para-phenylenediamine,
($a_2$): 2-aminophenol,
(b): 4-hydroxyindole;
($a_1$): para-aminophenol,
($a_2$): 2-aminophenol,
(b): 4-hydroxyindole;
($a_1$): para-toluylenediamine,
($a_2$): 2-aminophenol,
(b): 4-hydroxyindole;
($a_1$): 2,6-dimethyl-para-phenylenediamine,
($a_2$): 2-aminophenol,
(b): 4-hydroxyindole;
($a_1$): 2-β-hydroxyethyl-para-phenylenediamine,
($a_2$): 2-aminophenol,
(b): 4-hydroxyindole;
($a_1$): N,N-bis(β-hydroxyethyl)-para-phenylenediamine,
($a_2$): 2-aminophenol,
(b): 4-hydroxyindole;
($a_1$): 4-amino-3-methylphenol,
($a_2$): 2-aminophenol,
(b): 4-hydroxyindole;
($a_1$): 4-amino-3-fluorophenol,
($a_2$): 2-aminophenol,
(b): 4-hydroxyindole;
($a_1$): para-phenylenediamine,
($a_2$): para-aminophenol,
(b): 4-hydroxy-1-methylindole;
($a_1$): para-phenylenediamine,
($a_2$): 4-amino-3-methylphenol,
(b): 4-hydroxy-1-methylindole;
($a_1$): 2,6-dimethyl-para-phenylenediamine,
($a_2$): para-aminophenol,
(b): 4-hydroxy-1-methylindole;
($a_1$): 2,6-dimethyl-para-phenylenediamine,
($a_2$): 4-amino-3-methylphenol,
(b): 4-hydroxy-1-methylindole;
($a_1$): 2-methyl-para-phenylenediamine,
($a_2$): para-aminophenol,
(b): 4-hydroxy-1-methylindole;
($a_1$): 2-methyl-para-phenylenediamine,
($a_2$): 4-amino-3-methylphenol,
(b): 4-hydroxy-1-methylindole;
($a_1$): para-phenylenediamine,
($a_2$): 4-amino-3-fluorophenol,
(b): 4-hydroxy-1-methylindole;
($a_1$): para-phenylenediamine,
($a_2$): N,N'-bis(β-hydroxyethyl)-N,N'-bis(4'-aminophenyl)-1,3-diamino-2-propanol, (b): 4-hydroxyindole;
(a₁): para-phenylenediamine,
(a₂): N,N-bis(hydroxyethyl)-para-phenylenediamine
(b): 4-hydroxyindole;
(a₁): 2,6-dimethyl-para-phenylenediamine,
(a₂): N,N-bis(hydroxyethyl)-para-phenylenediamine
(b): 4-hydroxyindole;
(a₁): para-phenylenediamine,
(a₂): 4-amino-3-hydroxymethylphenol,
(b): 4-hydroxyindole;
(a₁): 2,6-dimethyl-para-phenylenediamine,
(a₂): 4-amino-3-hydroxymethylphenol,
(b): 4-hydroxyindole;
(a₁): para-phenylenediamine,
(a₂): N,N'-bis(β-hydroxyethyl)-N,N'-bis(4'-aminophenyl)-1,3-diamino-2-propanol,
(b): 4-hydroxy-1-methylindole;
(a₁): para-phenylenediamine,
(a₂): N,N-bis(hydroxyethyl)-para-phenylenediamine,
(b): 4-hydroxy-1-methylindole;
(a₁): 2,6-dimethyl-para-phenylenediamine,
(a₂): N,N-bis(hydroxyethyl)-para-phenylenediamine,
(b): 4-hydroxy-1-methylindole;
(a₁): para-phenylenediamine,
(a₂): 4-amino-3-hydroxymethylphenol,
(b): 4-hydroxy-1-methylindole;
(a₁): 2,6-dimethyl-para-phenylenediamine,
(a₂): 4-amino-3-hydroxymethylphenol,
(b): 4-hydroxy-1-methylindole.

15. A composition according to claim 1, wherein said at least two oxidation bases together represent from 0.0005 to 12% by weight relative to the total weight of the dye composition.

16. A composition according to claim 15, wherein said at least two oxidation bases together represent from 0.005 to 6% by weight relative to the total weight of the dye composition.

17. A composition according to claim 1, wherein said at least one indole coupler of formula (I) represents from 0.0001 to 5% by weight relative to the total weight of the dye composition.

18. A composition according to claim 17, wherein said at least one indole coupler of formula (I) represents from 0.005 to 3% by weight relative to the total weight of the dye composition.

19. A composition according to claim 1, wherein the medium which is suitable for dyeing comprises water or a mixture of water and at least one organic solvent selected from $C_1$–$C_4$ lower alkanols, glycerol, glycols and glycol ethers, aromatic alcohols, and mixtures thereof.

20. A composition according to claim 1, wherein said composition has a pH from 3 to 12.

21. A process for dyeing keratin fibers, said process comprising:
applying to said fibers a dye composition;
developing color at acidic, neutral or alkaline pH with an oxidizing agent which is added to the dye composition only at the time of application or which is present in an oxidizing composition that is applied:
(i) separately from the dye composition at the same time that said dyeing composition is applied to said fibers or
(ii) sequentially with the dye composition,
wherein said dye composition comprises:
a) at least two oxidation bases which are different from each other,
b) at least one indole coupler chosen from compounds of formula (I) and acid addition salts thereof:

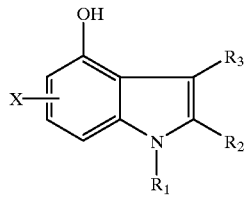

(I)

in which:
$R_1$ is chosen from a hydrogen atom and $C_1$–$C_4$ alkyl radicals,
$R_2$ and $R_3$, which may be identical or different, are chosen from a hydrogen atom, $C_1$–$C_4$ alkyl radicals, carboxyl radicals and ($C_1$–$C_4$)alkoxycarbonyl radicals,
X is chosen from a hydrogen atom, halogen atoms, $C_1$–$C_4$ alkyl radicals, $C_1$–$C_{18}$ alkoxy radicals, and acetylamino radicals,
wherein said at least two oxidation bases and said at least one coupler are present in said composition in a combined amount effective for the oxidation dyeing of keratin fibers.

22. A process according to claim 21, wherein said keratin fibers are human keratin fibers.

23. A process according to claim 22, wherein said human keratin fibers are hair.

24. A process according to claim 21, wherein said oxidizing agent is selected from hydrogen peroxide, urea peroxide, alkali metal bromates and persalts.

25. A process according to claim 24, wherein said persalts are perborates or persulphates.

26. A multi-compartment device, or multi-compartment dyeing kit, comprising a first compartment containing a dye composition as defined in claim 1 and a second compartment containing an oxidizing composition.

* * * * *